(12) United States Patent
Abraham

(10) Patent No.: US 7,771,736 B2
(45) Date of Patent: Aug. 10, 2010

(54) GLYPHOSATE FORMULATIONS AND THEIR USE FOR THE INHIBITION OF 5-ENOLPYRUVYLSHIKIMATE-3-PHOSPHATE SYNTHASE

(75) Inventor: William Abraham, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1466 days.

(21) Appl. No.: 10/652,684

(22) Filed: Aug. 29, 2003

(65) Prior Publication Data

US 2004/0077608 A1    Apr. 22, 2004

Related U.S. Application Data

(60) Provisional application No. 60/407,032, filed on Aug. 30, 2002.

(51) Int. Cl.
| | |
|---|---|
| A01N 57/02 | (2006.01) |
| A01N 25/00 | (2006.01) |
| A01N 57/18 | (2006.01) |
| A01N 37/00 | (2006.01) |
| A01N 37/12 | (2006.01) |
| A01N 37/44 | (2006.01) |
| A01N 35/08 | (2006.01) |

(52) U.S. Cl. .................. 424/405; 504/206; 514/563; 514/574

(58) Field of Classification Search ................ None
See application file for complete search history.

(56) References Cited

U.S. PATENT DOCUMENTS

| | | | |
|---|---|---|---|
| 3,903,297 A | | 9/1975 | Robert |
| 3,977,860 A | * | 8/1976 | Franz .................. 504/206 |
| 5,863,863 A | * | 1/1999 | Hasebe et al. ............ 504/358 |
| 5,877,186 A | | 3/1999 | Leef et al. |

OTHER PUBLICATIONS

MedlinePlus: Medical Encyclopedia: AIDS Apr. 14, 2004.*
Roberts, et al. Evidence for the Shikimate pathway in apicomplexan parasites Nature 1998, 393, 801-805.*
Pudney "Antimalarial: From Quinine to Atovaquone" Fifty Years of Antimicrobial: Past Perspectives and Future Trends (Cambridge Society for General Microbiology, 53rd Symposium, 1995) pp. 229-247.
Ream et al. "EPSP Synthase: Binding Studies Using Isothermal Titration Microcalorimetry and Equilibrium Dialysis and Their Implications for Ligand Recognition and Kinetic Mechanism" Biochemistry, vol. 31, No. 24 (1992) pp. 5528-5534.
Stokkermans et al. "Inhibition of *Taxoplasma gondii* Replication by Dinitroaniline Herbicides" Experimental Parasitology, vol. 84 (1996) pp. 355-370.
Hackstein et al. "Parasitic Apicomplexans Harbor a Chlorophyll a-D1 Complex, the Potential Target for Therapeutic Triazines" Parasitology Research, vol. 81 (1995) pp. 207-216.
Schmidt et al. "*Phylum Apicomplexa*: Malaria and Piroplasms" Foundations of Parasitology. St. Louis, Times Mirror/Mosby (1985) pp. 149, 173-178.
Du et al. "Characterization of *Streptococcus pneumoniae* 5-enolpyruvylshikimate 3-phosphate synthase and its activation by univalent cations" Eur. J. Biochem., vol. 267 (2000) pp. 222-227.
Roberts et al. "Evidence for the shikimate pathway in apicomplexan parasites" Nature, vol. 393 (Jun. 25, 1998) pp. 801-805.
Leech et al. "Mutagenesis of Active Site Residues in Type I Dehydroquinase from *Escherichia coli*" J. of Biological Chem., vol. 270, No. 43 (Oct. 27, 1995) pp. 25827-25836.
Ridley "Planting new targets for antiparasitic drugs" Nature Medicine, vol. 4, No. 8 (Aug. 1998) pp. 894-895.
Gallay et al. "Progress in cloning, expression and purification of 5-enolpyruvylshikimate-3-phosphate synthase from patohgens causing meningitis" Biochemical Society Transactions, vol. 25, No. 4 (Nov. 1997) p. S632.
Coombs et al. "Recent advances in the search for new anti-coccidial drugs" International Journal for Parasitology, vol. 32, No. 5 (May 2002) pp. 497-508.
Du et al. "Synergistic Inhibitor Binding to *Streptococcus pneumoniae* 5-Enolpyruvylshikimate-3-phosphate Synthase with Both Monovalent Cations and Substrate" Biochemistry, vol. 39, No. 33 (2000) pp. 10140-10146.
McConkey "Targeting the Shikimate Pathway in the Malaria Parasite *Plasmodium falciparum*" Antimicrobial Agents and Chemotherapy, vol. 43, No. 1 (Jan. 1999) pp. 175-177.

* cited by examiner

*Primary Examiner*—Ernst V Arnold
(74) *Attorney, Agent, or Firm*—Senniger Powers LLP; James E. Davis

(57) ABSTRACT

Protozoan parasites of the phylum Apicomplexa include some of the most important causative agents of human and animal diseases, in particular, malaria. The discovery that an organelle found inside parasites of this phylum probably stems from a plastid of plant origin has stimulated research on the effect of chemical herbicidal agents on Apicomplexa. Importantly, the growth of these parasites can be inhibited by the herbicide glyphosate, suggesting that the shikimate pathway will make a good target for the development of new anti-parasite agents. The present invention discloses the use of the herbicidal agent glyphosate in combination with the polyvalent anion oxalic acid for the prevention and therapy of these pathogenic infections.

8 Claims, 2 Drawing Sheets

GLYPHOSATE FORMULATIONS AND THEIR USE FOR THE INHIBITION OF 5-ENOLPYRUVYLSHIKIMATE-3-PHOSPHATE SYNTHASE

REFERENCE TO RELATED APPLICATIONS

This application claims the benefit of U.S. provisional application Ser. No. 60/407,032, filed Aug. 30, 2002, the entire disclosure of which is herein incorporated by reference.

FIELD OF INVENTION

This invention relates to the in vivo use of N-phosphonomethyl glycine, commonly known as glyphosate, or a salt, ester or other derivative thereof, in combination with a dicarboxylic acid or a derivative thereof, for the treatment of pathogenic infections, including infections of mammals by apicomplexan parasites.

BACKGROUND OF INVENTION

The shikimate pathway is an ancient pathway that is involved in primary and secondary metabolism and is found in all prokaryotes, many lower eukaryotes, and plants, but not in mammals. In primary metabolism, the function of the pathway is to provide the precursors for the production of the aromatic amino acids and para-aminobenzoic acid. The shikimate pathway includes the enzymes and metabolites formed by converting 3-Deoxy-D-arabino-heptulosonic 3-phosphate (DAHP) to chorismic acid, the trifurication point for the three pathways leading to the production of tryptophane, tyrosine, and phenylalanine.

The importance of the shikimate pathway to cell viability is illustrated by experiments that result in the disruption of enzyme function. In plants, the shikimate pathway enzyme, EPSP synthase, has been targeted by a chemical inhibitor strategy that has resulted in the commercially successful, broad range, post-emergent herbicide called glyphosate. Glyphosate inhibits the shikimic acid pathway, which leads to the biosynthesis of aromatic compounds including amino acids, plant hormones, and vitamins. Specifically, glyphosate inhibits the conversion of phosphoenolpyruvic acid (PEP) and 3-phosphoshikimic acid to 5-enolpyruvyl-3-phosphoshikimic acid by binding to the enzyme 5-enolpyruvyishikimate-3-phosphate synthase (hereinafter referred to as EPSP synthase or EPSPS).

In various microbial species, analysis of the shikimate pathway has been carried out genetically by the construction of mutants. When mutants of virulent prokaryotic or microbial eukaryotic species lacking enzymes at various steps in this pathway, the so-called aro⁻ mutants, are used to infect animals, their virulence is generally observed to be attenuated (Leech et al. 1995 J. Biol. Chem. 270:25827-25836 and Gunel-Ozcan et al. 1997. Microbial Pathogen 17:169-174). After infection with aro⁻ mutants of *S. typhimurium*, mice are resistant to further challenge with the wild type strain.

Recently, the shikimate pathway has been characterized in apicomplexan parasites such as *Toxoplasma gondii, Plasmodium falciparum* (malaria) and *Cryptosporidium parvum* (Roberts et al. 1998. Nature 393:801-805). In addition, Roberts et al. reported that the growth of these parasites can be inhibited by glyphosate.

The observations that both chemical and genetic inhibition of the shikimate pathway results in reduced cell viability has stimulated interest in the pathway as a possible target for drug therapy in acute microbial infection. It is likely that compounds which can inhibit the activity of shikimate enzymes will not cause cell death of the infecting microbe, but will result in attenuation in a manner analagous to the phenotype of shikimate pathway mutants. As antimicrobials, these compounds may be expected to induce stasis rather than cell lysis or death, allowing the infection to be cleared by the host's immune system. Such an outcome is desirable as it will ameliorate the absolute selective pressure to select for the growth of resistant mutants which would inevitably be the case if the compounds used caused cell death. Additionally this strategy may also result in a degree of immune protection which may prevent reinfection. As efficacious compounds are unlikely to kill any infecting microorganisms, then the risks of toxic shock caused by, for example, bacterial protein and cellular debris will be minimized when treatment is administered.

Protozoan parasites of the phylum Apicomplexa include the causative agents of the human disease malaria, as well as the agents of cattle diseases such as Texas cattle fever and East Coast fever. Furthermore, the causative agent of the human disease toxoplasmosis, *Toxoplasma gondii*, is also found in this phylum (Schmidt, G. D. and Roberts, L. S. 1985. Foundations of Parasitology. St. Louis, Times Mirror/Mosby, pp. 149, 173-178).

Malaria is one of the most important diseases of mankind. Two billion people are at risk of contracting malaria; over 200 million people are infected by the disease, and 3 million people die of malarial infection each year. The disease is caused by four species of plasmodia, *Plasmodium falciparum, Plasmodium vivax, Plasmodium ovale*, and *Plasmodium malariae*. Strains of the most common and most severe causative agent, *P. falciparum*, have developed resistance to many of the current drugs used in treatment, and drug resistance has also been reported in *P. vivax* (Pudney, M. "Antimalarial: From Quinine to Atovaquone" in: Hunter, P. A., Darby, G. K. and Russell, N. J. Fifty Years of Antimicrobial: Past Perspectives and Future Trends (Cambridge, Society for General Microbiology, 53rd Symposium, 1995), pp. 229-247).

Chemical agents belonging to the triazine class of herbicides have been suggested as potential therapeutic agents. Such activity against some apicomplexan parasites is thought to result from interaction of the herbicide with the D1 protein of the photosynthetic reaction center of organelles of the parasites (Hackstein, J. H. P. et al. 1995. Parasitology Research 81:207-216). In addition, dinitroaniline herbicides known to be inhibitors of plant microtubules also inhibit some apicomplexan parasites (Stokkermans, T. J. W. et al. 1996. Experimental Parasitology 84:355-370). Others have nominated herbicidal agents which inhibit carotenoid synthesis or certain herbicidal agents which inhibit fatty acid synthesis as inhibitors of apicomplexan parasites (see U.S. Pat. No. 5,877,186).

Recently, oxalic acid, a dicarboxylic acid, was shown to enhance the herbicidal efficacy of glyphosate (See U.S. Pat. No. 5,863,863). The mode of action of oxalic acid, however, was attributed to its ability to interact with cationic amine surfactants and oxalic acid was formulated in the form of an enhancer composition containing oxalic acid and cationic surfactants, which was then used to dilute commercial glyphosate formulations. Oxalic acid and other polyvalent anions that are good chelators have been shown to enhance glyphosate performance by sequestering bivalent cations.

However, use of complexing agents as additives to glyphosate has been reported in the literature.

SUMMARY OF INVENTION

Among the various aspects of the present invention is a method for treating a subject infected or susceptible to an infection by a pathogen containing the enzyme 5-enolpyruvoylshikimate-3-phosphate synthase. Briefly, therefore, the present invention is directed to a method for therapeutically or prophylactically treating a subject for a pathogenic infection, the method comprising administering to the subject glyphosate or a salt, ester or other derivative thereof and a dicarboxylic acid or a derivative thereof.

The present invention is further directed to formulations for the treatment of pathogenic infections in a subject in need thereof. The formulation comprises a glyphosate or a salt, ester or other derivative thereof, a dicarboxylic acid or a derivative thereof, and a pharmaceutically acceptable vehicle.

DESCRIPTION OF THE PREFERRED EMBODIEMENTS

Numerous publications describe the structure of EPSPS and the conformational changes that occur during the binding of S3P, a substrate, and glyphosate, an inhibitor to EPSPS. This enzyme consists of two distinct hemispherical domains connected by a double-stranded hinge. The active site is believed to reside in the inter-domain cleft or the hinge region. There is a gradient of positive charge that guides the substrate and inhibitor molecules each of which are polyvalent anions to the active site. The conformational change from the open to the closed form of the enzyme is believed to occur through a combination of electrostatic and H-bonding interactions between the anionic ligands and cationic active site of the enzyme. The key amino acid residues involved in these interactions are basic residues (such as arginine, histidine, and lysine). Since glyphosate is a powerful inhibitor of EPSPS, it is generally believed that binding of glyphosate to S3P-EPSPS is very tight. It has been shown that glyphosate binds to the S3P-EPSPS complex better than the native enzyme (Ream, J. E., et al. (1992) Biochemistry 31:5528-5534).

Due to this high binding efficacy of glyphosate to the target enzyme-substrate complex and due to the excellent inhibitory efficacy of glyphosate and its herbicidal efficacy, efforts have been directed toward efficient delivery of glyphosate to the target site and not much attention has been paid to the efficacy of the binding process itself.

Figure 1:
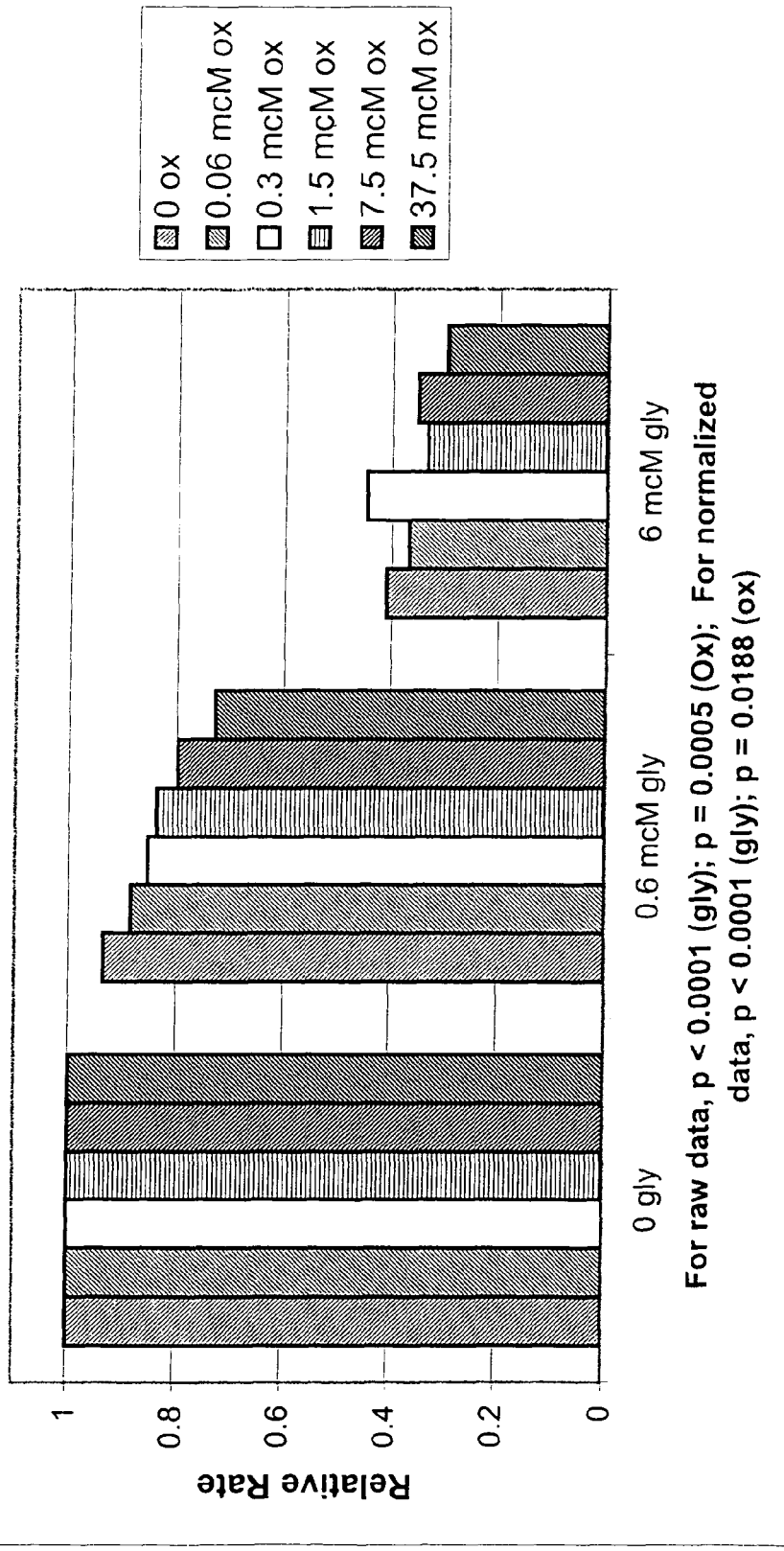
FIG. 1—Oxalic acid was shown to enhance the inhibition of EPSPS by glyphosate by measuring the rate of the catalytic activity of maize EPSPS on S3P and PEP. These observations indicated that the major mode of action of oxalic acid is at the enzyme level.

Surprisingly, however, it has been found that the inhibitory effect of glyphosate on EPSPS can be increased by the concomitant use of a dicarboxylic acid component, such as oxalic acid, or a derivative thereof. Without being bound to any particular theory, a polyvalent anionic species such as oxalate is believed to act as molecular staples whereby through a combination of electrostatic interactions with basic amino acid residues around the active site, the closed conformation of the enzyme is made more stable. This would lower the $K_d$ of the S3P-EPSPS-glyphosate ternary complex. Data reported in the literature from x-ray crystallography have clearly identified the 427 amino acid side chains. Each of the six α-helices in the top domain and four of the six α-helices in the lower domain are capped with basic amino acid residues. Interaction of polyvalent anions of the proper steric requirement with these basic amino acid residues on the surface of the two domains of the enzyme through electrostatic interaction would produce a stapling action. Such stapling action is possible only on an already closed, albeit partially closed conformation of the ternary complex of S3P-EPSPS-glyphosate. For example, oxalate was shown to enhance the inhibition of EPSPS by glyphosate as well as its herbicidal efficacy in whole plants. Oxalic acid was shown to enhance the inhibition of EPSPS by glyphosate by measuring the rate of the catalytic activity of maize EPSPS on S3P and PEP. These observations indicate that the major mode of action of oxalic acid is at the enzyme level (see FIG. 1).

Based on enzyme studies and whole plant response, oxalic acid by itself does not have any herbicidal property. Thus, it appears that one or more oxalate molecules act as molecular staple(s), making the S3P-EPSPS-glyphosate complex tighter, and do not have any inhibitory effect on the enzyme on their own. This would require very specific orientation of the anionic moieties as well as steric requirements. Thus, for example, oxalate enhanced the enzyme binding of glyphosate, but citrate did not, even though citrate is a trivalent ion with an additional OH moiety for H-bonding with the amino acid residues.

Thus, the stapling action does not depend on the absolute number of the anionic sites as much as it does on the suitable dimension of the molecule. Any such compound with stapling action to close the ternary complex tighter, thereby enhancing the inhibition of the enzyme is claimed under this invention. The novelty here is the precise requirement for such a compound that would make it enhance the inhibition of the enzyme.

The key distinction here from the published literature is the requirement that the polyvalent anions should be able to enhance the inhibition of EPSPS by glyphosate by interaction with the target enzyme, presumably through this stapling mechanism. While most of the polyvalent anions are metal chelators, they do not elicit the same response on the enzyme as suggested in the current invention. This was clearly established by comparing oxalate and citrate in the enzyme studies.

Figure 2:
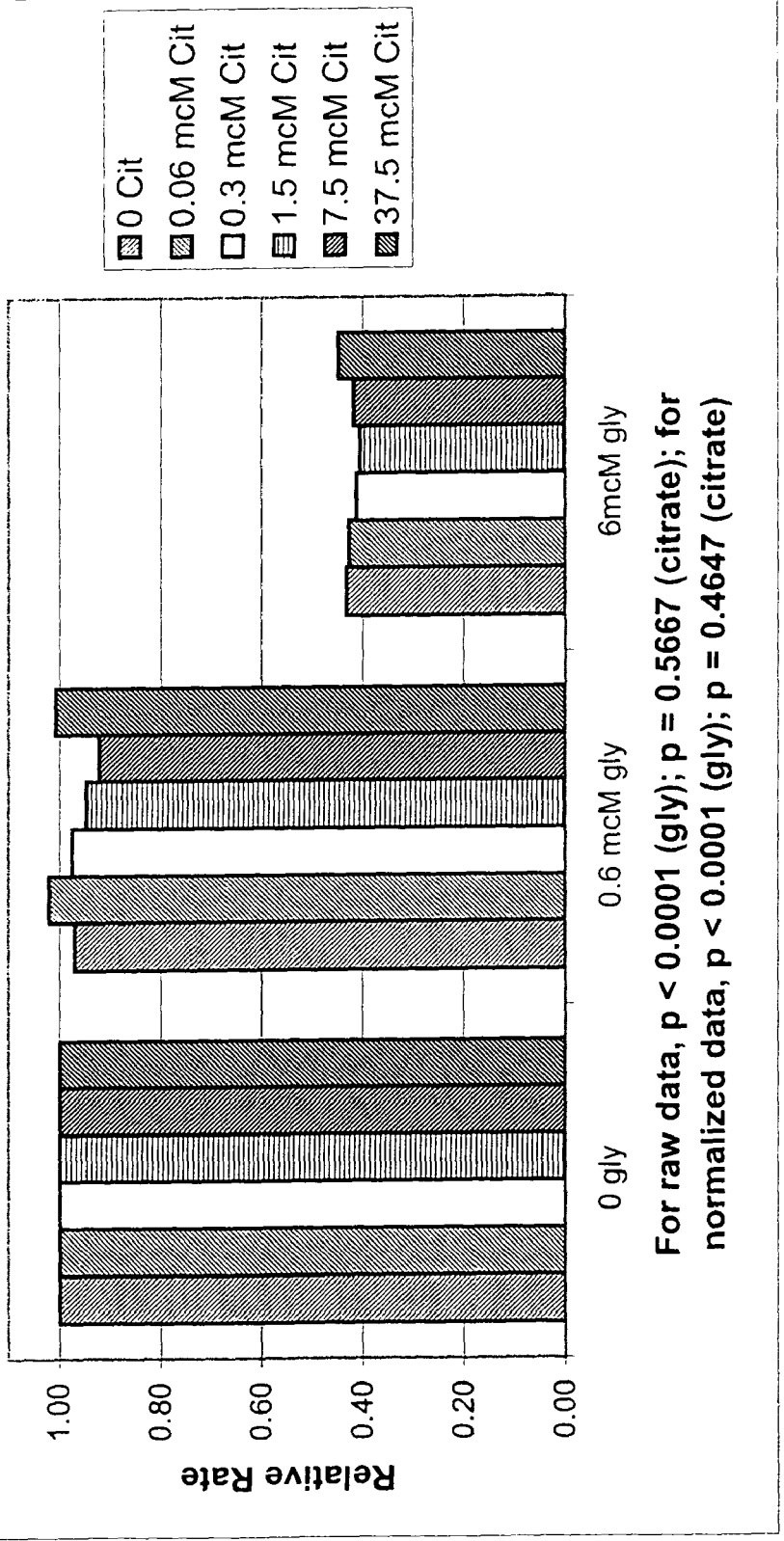
FIG. 2—Despite the high affinity of citric acid to metal ions compared to oxalic acid (an order of magnitude higher), citric acid failed to show enhancement of glyphosate efficacy on different weed species. Also citric acid did not have any effect on EPSPS inhibition by glyphosate.

The ability of citric acid and oxalic acid to bind bivalent metal ions is shown in Table 1. Despite the high affinity of citric acid to metal ions compared to oxalic acid (an order of magnitude higher), citric acid failed to show enhancement of glyphosate efficacy on different weed species. Also citric acid did not have any effect on EPSPS inhibition by glyphosate (see FIG. 2).

TABLE 1

| Chelator | Metal Ion | Log K (Binding Constant) |
| --- | --- | --- |
| Citric Acid | $Ca^{2+}$ | 3.45 |
|  | $Mg^{2+}$ | 3.45 |
| Oxalic Acid | $Ca^{2+}$ | 2.46 |
|  | $Mg^{2+}$ | 2.76 |

The envisioned molecular staples are dicarboxylic acids that have the suitable steric and conformational property to bind to the cationic moieties on the surface of the two lobes of EPSPS. This would make the S3P-EPSPS-glyphosate complex more stable.

In accordance with one aspect of the present invention, therefore, a subject in need of or which would benefit from prophylactic or therapeutic treatment for a pathogenic infection is administered glyphosate (in the form of its acid, a prodrug thereof, a salt thereof, an ester thereof or other derivative thereof) and a dicarboxylic acid (in the form of its acid, a salt thereof, or other derivative thereof).

Suitable dicarboxylic acids that may be added to the formulations include oxalic acid, malonic acid, succinic acid, malic acid, tartaric acid, fumaric acid, maleic acid, glutaric acid, dimethylglutaric acid, adipic acid, trimethyladipic acid, pimelic acid, tartronic acid, suberic acid, azelaic acid, sebacic acid, 1,12-dodecanedioic acid, 1,13-tridecanedioic acid, glutamic acid, phthalic acid, isophthalic acid, or terephthalic acid, an anhydride, ester, amide, halide, salt or precursor of any of said acids or mixtures of any of said acids, anhydrides, esters, amides, halides, salts or precursors with oxalic acid being preferred. Suitable salts include, for example, alkali metal salts such as sodium and potassium salts, alkanolamine salts and alkylamine salts such as IPA. Preferred salts include potassium oxalate, dipotassium oxalate, sodium oxalate, disodium oxalate, diammonium oxalate, diethanolamine oxalate, dimethylamine oxalate, alkanolamine salts of oxalic acid, and lower alkylamine salts of oxalic acid.

Precursors of dicarboxylic acids can be used as the dicarboxylic acid component of the compositions of the invention. Terminally functionalized hydroxyacids, oxoacids, $\alpha,\omega$-dihydroxyalkanes, dinitriles, and dioxoalkanes are easily oxidized to dioic acids. $\alpha,\omega$-Aminoacids, haloacids, and dihalides are hydrolyzable to hydroxyacids or dihydroxides which are then oxidized. Precursors for use in the invention include, for example, oxalic acid precursors (glycolic acid, glyoxylic acid (and salts, e.g., oxaloacetate), ethylene glycol, glyoxal, 1,2-dihaloethane), adipic acid precursors (e.g., $\alpha$-aminoadipic acid, cyclohexanol, cyclohexanone, cyclohexane), malonic acid precursors (e.g., malic acid, malonic dialdehyde, methylmalonic acid, cyanoacetic acid, diethyl malonate, malonyl Coenzyme A, acetyl CoA, acetate, butyrate), malic acid precursors (ketoglutaric acid, 2-oxoglutaric), succinic acid precursors (e.g., malic acid, malate, maleic acid, ketoglutaric acid, succinic acid dimethyl ester, succinic dialdehyde, L-glutamate, oxaloacetate, fumarate), and glutaric acid precursors (e.g., glutaric dialdehyde, glutaronitrile, cyclopentane, cyclopentanone, lysine, tryptophan, hemiamido glutarate, amidomethyl glutarate).

Susceptible Pathogens

All organisms that contain the enzyme EPSPS should be susceptible to the treatment method of the present invention. These organisms include, but are not limited to all species of the Phylum Apicomplexa, including but not limited to *Toxoplasma gondii, Cryptosporidium parvum, Neospora caninum, Eimeria* spp., *Isospora* spp., including but not limited to *I. belli, Theileria* spp., including but not limited to *T. parva* and *T. annulata, Plasmodium* spp., including but not limited to *P. falciparum, P. vivax, P. malariae* and *P. ovale*, and *Babesia* spp., including but not limited to *B. microti, B. divergens, B. canis, B. bigemina, B. bovis, B. ovis, B. caballi, B. equi, B. gibsoni* and *B. felis.*

Susceptible organisms include, but are not limited to all species of the Family Neisseriaceae, including but not limited to *Neisseria meningitidis* and *Neisseria gonorrhoeae, Moraxella* spp., including but not limited to *M. lacumata, M. nonliquefaciens, M. urethralis, M. catarrhalis*, and *M. bovis, Klingella* spp., including but not limited to *K. dentrificans* and *K. kingae* and *Eikenella* spp., including but not limited to *E. corrodens.*

Susceptible organisms include, but are not limited to all species of the Family Enterobacteriaceae, including but not limited to *Escherichia coli* and *Edwardsiella ictaluri, Klebsiella* spp., including but not limited to *K. pneumonia* and *K. oxytoca, Salmonella* spp., including but not limited to *S. typhimurium, S. typhi, S. paratyphi, S. enteritidis* and *S. cholerasuis, Serratia* spp., including but not limited to *S. marcesans* and *S. liquifaciens, Shigella* spp., including but not limited to *S. dysenteriae, S. flexneri, S. boydii* and *S. sonnei, Yersinia* spp., including but not limited to *Y. enterocolitica, Y. pestis, Y. pseudotuberculosis* and *Y. ruckeri, Citrobacter* spp., including but not limited to *C. freundii* and *C. diversus, Enterobacter* spp., including but not limited to *E. aerogenes, E. agglomerans* and *E. cloacae, Morganella* spp., including but not limited to *M. morganii, Proteus* spp., including but not limited to *P. mirabilis* and *P. vulgaris* and *Providencia* spp., including but not limited to *P. alcalifaciens, P. rettgeri* and *P. stuartii.*

Susceptible organisms include, but are not limited to all species of the Family Pasteurellaceae, including but not limited to *Pasteurella multocida* and *Actinobacillus pleuropneumoniae, Haemophilus* spp., including but not limited to *Haemophilus influenzae, Haemophilus parainfluenzae, Haemophilus ducreyi, Haemophilus aphrophilus* and *Haemophilus aegyptius.*

Susceptible organisms include, but are not limited to all species of the Family Mycobacteriaceae, including but not limited to *Mycobacterium* spp., including but not limited to *M. tuberculosis, M. bovis, M. africanum, M. microtti, M. leprae, M. kansasii, M. avium-intracellulare, M. scrofulaceum, M. ulcerans* and *M. marinum.*

Susceptible organisms include, but are not limited to all species of the Family Nocardiaceae, including but not limited to *Nocardia* spp., including but not limited to *N. asteroides, N. brasiliensis* and *N. caviae.*

Susceptible organisms include, but are not limited to all species of the Family Brucellaceae, including but not limited to *Brucella* spp., including but not limited to *B. abortus, B. suis, B. melitensis* and *B. canis.*

Susceptible organisms include, but are not limited to all species of the Family Trypanosomatida, including but not limited to *Leishmania* spp., including but not *L. tropica, L. major, L. donovani, L. braziliensis* and *L. mexicana.*

Susceptible organisms include, but are not limited to all species of the Family Streptococcaceae, including but not limited to *Streptococcus* spp., including but not limited to *S. pneumoniae, S. pyogenes, S. agalactiae, S. mutans, S. milleri, S. sanguis, S. anginosus, S. bovis, S. equisimilis, S. salivarius* and *S. mitis.*

Susceptible organisms include, but are not limited to all species of the Family Alcaligenaceae, including but not limited to *Bordetella* spp., including but not limited to *B. pertusis, B. parapertusis, B. brochiseptica, B. avium* and *B. hinzii.*

Susceptible organisms include, but are not limited to all species of the Family Micrococcaceae, including but not limited to *Staphylococcus* spp., including but not limited to *S. aureus, S. epidermidis, S. saprophiticus, S. lugdunensis, S. haemolyticus, S. warneri, S. schleiferi* and *S. intermedius.*

Susceptible organisms include, but are not limited to all species of the Family Trichocomaceae, including but not limited to *Aspergillus* spp., including but not limited to *A. fumigatus, A. flavus, A. amstelodami, A. avenaceus, A. candidus, A. cameus, A. caesiellus, A. clavatus, A. glaucus, A.*

*granulosus, A. nidulans, A. niger, A. oryzae, A. quadrilineatus, A. restrictus, A. sydowi, A. terreus, A. ustus* and *A. versicolor.*

Susceptible organisms include, but are not limited to all species of the Family Bacillaceae, including but not limited to *Bacillus* spp., including but not limited to *B. anthracis, B. subtilis* and *B. halodurans* and *Clostridium* spp., including but not limited to *C. perfringens, C. tetani, C. difficile* and *C. botulinum.*

Susceptible organisms include, but are not limited to all species of the Family Chlamydiaceae, including but not limited to *Chlamydia* spp., including but not limited to *C. trachomatis* and *C. pneumoniae* and *Chlamydophila* spp., including but not limited to *C. pneumoniae, C. abortus* and *C. psittaci.*

Susceptible organisms include, but are not limited to all species of the Family Listeriaceae, including but not limited to *Listeria* spp., including but not limited to *L. monocytogenes, L. innocua* and *L. ivanovii.*

Susceptible organisms include, but are not limited to all species of the Family Pseudomonadaceae, including but not limited to *Pseudomonas aeruginosa.*

Susceptible organisms include, but are not limited to all species of the Family Enterococcaceae, including but not limited to *Enterococcus faecalis* and *Enterococcus faecium.*

Susceptible organisms include, but are not limited to all species of the Family Cardiobacteriaceae, including but not limited to *Dichelobacter nodosus.*

Susceptible organisms include, but are not limited to all species of the Family Campylobacteriaceae, including but not limited to *Campylobacter jejuni.*

Susceptible organisms include, but are not limited to all species of the Family Aeromonadaceae, including but not limited to *Aeromonas hydrophila* and *Aeromonas salmonicida.*

Susceptible organisms include Helicobacterpylori, *Candida albicans* and *Pneumocystis carinii.*

Dosage

Any suitable dosage may be administered in the methods of the present invention. The composition or salt or prodrug thereof chosen for a particular application, the carrier and the amount will vary widely depending on the species of the warm blooded animal or human or the particular infection being treated, and depending upon the effective inhibitory concentrations observed in trial studies. The dosage administered will, of course, vary depending upon known factors, such as the pharmacodynamic characteristics of the particular composition, salt, or combination and its mode and route of administration; the age, health, or weight of the subject; the nature and extent of symptoms; the metabolic characteristics of the drug and patient, the kind of concurrent treatment; the frequency of treatment; or the effect desired.

Generally a dosage of as little as about 1-2 milligram (mg) per kilogram (kg) of body weight is suitable, but preferably as little as 10 mg/kg and up to about 10,000 mg/kg of each of the glyphosate source and the dicarboxylic acid component may be used. Typically, a dosage from 15 mg/kg to about 5000 mg/kg of each is used. More typically, the dose is between 150 mg/kg to about 1000 mg/kg although any range of doses can be used. Generally, a composition, salt thereof, prodrug thereof, or combination of the present invention can be administered on a daily basis one or more times a day, or one to four times a week, either in a single dose or separate doses during the day. Twice-weekly dosing over a period of at least several weeks is preferred, and often dosing will be continued over extended periods of time and possibly for the lifetime of the patient. The dosage and the dosage regimen will vary depending on the ability of the patient to sustain the desired and effective plasma levels of the compounds of the present invention, or salt or prodrug thereof, in the blood.

The compound, salt thereof, prodrug thereof, or combination may be micronized or powdered so that it is more easily dispersed and solubilized by the body. Processes for grinding or pulverizing drugs are well known in the art. For example, a hammer mill or similar milling device can be used. The preferred particle size is less than about 100 m and preferably less than 50 m.

Intravenously, the most preferred doses may range from about 1 to about 10 mg/kg/minute during a constant rate infusion.

The compositions and salts and prodrugs thereof of the present invention may be administered in a unit dosage form which may be prepared by any methods known to one of skill in the art in light of the present disclosure. Unit dosages may include from 1 milligram to 1000 milligrams of active ingredient. Preferably the dosage unit will contain from about 10 mg to about 500 mg active ingredient. The active ingredient is generally present in an amount of about 0.5% to about 95% by weight based on the total weight of the dosage unit.

For intravenous use, preferred dosages may range from about 1 to about 10 mg/kg/minute during a constant rate infusion.

A dosage unit may comprise a single compound, or mixtures thereof, with other compounds. The dosage unit may comprise diluents, extenders, carriers, liposomes, or the like. The unit may be in solid or gel form such as pills, tablets, capsules and the like or in liquid form suitable for oral, rectal, topical, intravenous injection or parenteral administration or injection into or around the treatment site.

Formulations

Formulations of the present invention include the compound of the present invention, a salt thereof or a prodrug thereof and, optionally, another pharmaceutically active agent, such as a chemotherapeutic agent and, optionally, a potentiator generally mixed with a pharmaceutically acceptable carrier. A "pharmaceutical carrier" is a pharmaceutically acceptable solvent, suspending agent or vehicle for delivering a compound of the present invention to the animal or human. The carrier may be liquid or solid and is selected with the planned manner of administration in mind. A "pharmaceutically acceptable" component is one that is suitable for use with humans and/or animals without undue adverse side effects (such as toxicity, irritation, and allergic response) commensurate with a reasonable benefit/risk ratio.

Oral formulations suitable for use in the practice of the present invention include capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. The compounds of the present invention may also be presented as a bolus, electuary, or paste.

Generally, formulations are prepared by uniformly mixing the active ingredient with liquid carriers or finely divided solid carriers or both, and then if necessary shaping the product. A pharmaceutical carrier is selected on the basis of the chosen route of administration and standard pharmaceutical practice. Each carrier must be "acceptable" in the sense of being compatible with the other ingredients of the formulation and not injurious to the subject. This carrier can be a solid or liquid and the type is generally chosen based on the type of administration being used. Examples of suitable solid carriers include lactose, sucrose, gelatin, agar and bulk powders.

Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also preferred carriers.

The formulations for oral administration may comprise a non-toxic, pharmaceutically acceptable, inert carrier such as lactose, starch, sucrose, glucose, methyl cellulose, magnesium stearate, dicalcium phosphate, calcium sulfate, mannitol, sorbitol, cyclodextrin, cyclodextrin derivatives, or the like.

Capsule or tablets can be easily formulated and can be made easy to swallow or chew. Tablets may contain suitable carriers, binders, lubricants, diluents, disintegrating agents, coloring agents, flavoring agents, flow-inducing agents, or melting agents. A tablet may be made by compression or molding, optionally with one or more additional ingredients. Compressed tables may be prepared by compressing the active ingredient in a free flowing form (e.g., powder, granules) optionally mixed with a binder (e.g., gelatin, hydroxypropylmethylcellulose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, or the like. Lubricants used in these dosage forms include sodium oleate, sodium stearate, magnesium stearate, sodium benzoate, sodium acetate, sodium chloride, or the like. Disintegrators include, for example, starch, methyl cellulose, agar, bentonite, xanthan gum, or the like. Molded tablets may be made by molding in a suitable machine a mixture of the powdered active ingredient moistened with an inert liquid diluent.

The tablets may optionally be coated or scored and may be formulated so as to provide slow- or controlled-release of the active ingredient. Tablets may also optionally be provided with an enteric coating to provide release in parts of the gut other than the stomach.

Exemplary pharmaceutically acceptable carriers and excipients that may be used to formulate oral dosage forms of the present invention are described in U.S. Pat. No. 3,903,297 to Robert, issued Sep. 2, 1975, incorporated by reference herein. Techniques and compositions for making dosage forms useful in the present invention are described in the following references: 7 *Modern Pharmaceutics*, Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition (1976).

Formulations suitable for topical administration in the mouth wherein the active ingredient is dissolved or suspended in a suitable carrier include lozenges which may comprise the active ingredient in a flavored carrier, usually sucrose and acacia or tragacanth; gelatin, glycerin, or sucrose and acacia; and mouthwashes comprising the active ingredient in a suitable liquid carrier.

Topical applications for administration according to the method of the present invention include ointments, cream, suspensions, lotions, powder, solutions, pastes, gels, spray, aerosol or oil. Alternately, a formulation may comprise a transdermal patch or dressing such as a bandage impregnated with an active ingredient and optionally one or more carriers or diluents. To be administered in the form of a transdermal delivery system, the dosage administration will, of course, be continuous rather than intermittent throughout the dosage regimen.

The topical formulations may desirably include a compound that enhances absorption or penetration of the active ingredient through the skin or other affected areas. Examples of such dermal penetration enhancers include dimethylsulfoxide and related analogues.

The oil phase of an emulsion used to treat subjects in the present invention may be constituted from ingredients known to one of skill in the art in light of the present disclosure. An emulsion may comprise one or more emulsifiers. For example, an oily phase may comprise at least one emulsifier with a fat or an oil, with both a fat and an oil, or a hydrophilic emulsifier may be included together with a lipophilic emulsifier that acts as a stabilizer. Together, the emulsifier(s), with or without stabilizer(s), make up an emulsifying wax, and the wax together with the oil and/or fat make up the emulsifying ointment base that forms the oily dispersed phase of the cream formulations.

Emulsifiers and emulsion stabilizers suitable for use in the formulation include Tween 60, Span 80, cetosteryl alcohol, myristyl alcohol, glyceryl monostearate and sodium lauryl sulphate, paraffin, straight or branched chain, mono- or dibasic alkyl esters, mineral oil. The choice of suitable oils or fats for the formulation is based on achieving the desired cosmetic properties, the properties required and compatibility with the active ingredient.

Compounds of the present invention may also be administered vaginally, for example, as pessaries, tampons, creams, gels, pastes, foams or spray formulations containing appropriate carriers in addition to the active ingredient. Such carriers are known in the art in light of the present disclosure.

Formulations for rectal administration may be presented as a suppository with a suitable base comprising, for example, cocoa butter or a salicylate. Formulations suitable for nasal administration may be administered in a liquid form, for example, nasal spray, nasal drops, or by aerosol administration by nebulizer, including aqueous or oily solutions of the active ingredient. Formulations for nasal administration, wherein the carrier is a solid, include a coarse powder having a particle size, for example, of less than about 100 microns, preferably less than about 50 microns, which is administered in the manner in which snuff is taken, i.e., by rapid inhalation through the nasal passage from a container of the powder held close up to the nose.

Formulations suitable for parenteral administration include aqueous and non-aqueous formulations isotonic with the blood of the intended recipient; and aqueous and non-aqueous sterile suspensions which may include suspending systems designed to target the compound to blood components or one or more organs. The formulations may be presented in unit-dose or multi-dose sealed containers, for example, ampoules or vials. Extemporaneous injections solutions and suspensions may be prepared from sterile powders, granules and tablets of the kind previously described. Parenteral and intravenous forms may also include minerals and other materials to make them compatible with the type of injection or delivery system chosen.

In general, water, a suitable oil, saline, aqueous dextrose (glucose), or related sugar solutions and glycols such as propylene glycol or polyethylene glycols are suitable carriers for parenteral solutions. Solutions for parenteral administration preferably contain a water soluble salt of the active ingredient, suitable stabilizing agents and, if necessary, buffer substances. Antioxidizing agents, such as sodium bisulfite, sodium sulfite, or ascorbic acid, either alone or combined, are suitable stabilizing agents. Also used are citric acid salts thereof, or sodium EDTA. In addition, parenteral solutions may contain preservatives, such as benzalkonium chloride, methyl- or propyl-paraben, or chlorobutanol.

The present invention additionally contemplates administering compounds of the herein described invention for use in the form of veterinary formulations, which may be prepared, for example, by methods that are conventional in the art in light of the present disclosure.

Useful pharmaceutical dosage formulations for administration of the compounds of the present invention are illustrated as follows:

Capsules: A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules: A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets: A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 1 1 milligrams of starch and 98.8 milligrams of lactose. Appropriate coatings can be applied to increase palatability or delay absorption.

Injectable: A parenteral composition suitable for administration by injection is prepared by stirring 1.5% by weight of active ingredient in 10% by volume propylene glycol and water. The solution is made isotonic with sodium chloride and sterilized.

Suspension: An aqueous suspension is prepared for oral administration so that each 5 ml contains 100 mg of finely divided active ingredient, 200 mg of sodium carboxymethyl cellulose, 5 mg of sodium benzoate, 1.0 g of sorbitol solution, U.S.P., and 0.025 ml of vanillin.

Compounds of the present invention may be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may be coupled with soluble polymers as targetable drug carriers. Such polymers can include polyvinylpyrrolidone, pyran copolymer, polyhydroxylpropylmethacrylamide-phenol, polyhydroxyethylaspartamidephenol, or polyethyleneoxidepolylysine substituted with palmitoyl residues. Furthermore, the compounds of the present invention can be coupled to a class of biodegradable polymers useful in achieving controlled release of a drug, for example, polylactic acid, polyglycolic acid, copolymers of polylactic and polyglycolic acid; polyepsilon caprolactone, polyhydroxy butyric acid, polyorthoesters, polyacetals, polydihydropyrans, polycyanoacylates, and crosslinked or amphipathic block copolymers of hydrogels.

Method of Treatment

Treatment includes administering a therapeutically effective amount of the compositions of the present invention in a form described hereinabove, to a subject in need of treatment.

Compositions of the present invention can be administered by any means that produces contact of the active agent with the agent's site of action in the body, for example, suitable means including, but not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration. They can be administered by any conventional means available for use in conjunction with pharmaceuticals, either as individual therapeutic agents or in a combination of therapeutics. Preferably, composition of the present invention is administered as a pharmaceutical formulation comprising at least one compound of the present invention, as defined above, together with one or more pharmaceutically acceptable carriers. It can be co-administered in the form of a tablet or capsule, as an agglomerated powder, or in a liquid form, or as a liposome.

The preferred route will vary with the condition and age of the recipient, the nature of the disorder being treated, or the severity of disorder. It is believed that oral administration, or parenteral treatment is the preferred method of administering the composition to subjects in need thereof.

Combination Therapy

Combination therapy is intended to include any chemically compatible combination of a composition of the present invention with other compounds or compositions outside of the present invention, as long as the combination does not eliminate the activity of the compound of the present invention.

Combination therapy can be sequential, that is the treatment with one agent first and then the second agent, or it can be treatment with both agents at the same time. The sequential therapy can be within a reasonable time after the completion of the first therapy before beginning the second therapy. The treatment with both agents at the same time can be in the same daily dose or in separate doses. For example, treatment with one agent on day 1 and the other on day 2. The exact regimen will depend on the disorder being treated, the severity of the disorder, and the response to the treatment.

It is to be understood that the present invention has been described in detail by way of illustration and example in order to acquaint others skilled in the art with the invention, its principles, and its practical application. Further, the specific embodiments of the present invention as set forth are not intended to be exhaustive or to limit the invention, and that many alternatives, modifications, and variations will be apparent to those skilled in the art in light of the foregoing examples and detailed description. Accordingly, this invention is intended to embrace all such alternatives, modifications, and variations that fall within the spirit and scope of the following claims. While some of the examples and descriptions above include some conclusions about the way the invention may function, the inventors do not intend to be bound by those conclusions and functions, but put them forth only as possible explanations in light of current understanding.

This invention will be better understood by reference to the following Examples, which are intended to merely illustrate the best mode now known for practicing the invention. The scope of the invention is not to be considered limited thereto, however.

EXAMPLES

These examples assessed the enzyme activity of maize EPSPS with increasing concentrations of oxalate (0, 0.06 mcM, 0.3 mcM, 1.5 mcM, 7.5 mcM and 37.5 mcM) in the presence and absence of glyphosate. Three different conditions (0, 0.6 mcM, and 6 mcM glyphosate) were studied. The assay consisted of incubating enzyme (9 mcg/mL final concentration in the assay) with S3P and $^{14}$C-PEP. The conversion of labeled substrate to 5-enol-[$^{14}$C]-pyruvylshikimate-3-phosphate was determined by HPLC radioassay.

Initial velocities were calculated by multiplying fractional turnover per unit time by the initial concentration of the labeled substrate. The data are expressed as relative rates of the enzyme, where relative rate is the reaction rate at a given condition normalized to similar reaction with zero glyphosate.

Example 1

Effect of Oxalate on EPSPS Inhibition

Oxalate was shown to enhance the inhibition of EPSPS by glyphosate as well as its herbicidal efficacy in whole plants. Oxalic acid was shown to enhance the inhibition of EPSPS by glyphosate by measuring the rate of the catalytic activity of maize EPSPS on S3P and PEP. These observations indicated that the major mode of action of oxalic acid is at the enzyme level (see FIG. 1).

Example 2

Effect of Citrate on EPSPS Inhibition

The ability of citric acid and oxalic acid to bind bivalent metal ions is shown in Table 1. Despite the high affinity of citric acid to metal ions compared to oxalic acid (an order of magnitude higher), citric acid failed to show enhancement of glyphosate efficacy on different weed species. Also citric acid did not have any effect on EPSPS inhibition by glyphosate (see FIG. 2).

The present invention is not limited to the above embodiments and can be variously modified. The above description of the preferred embodiment is intended only to acquaint others skilled in the art with the invention, its principles, and its practical application so that others skilled in the art may adapt and apply the invention in its numerous forms, as may be best suited to the requirements of a particular use.

I claim:

1. A process of treating an animal subject for a pathogenic infection, wherein the infection is by a pathogen containing the enzyme 5-enolpyruvoylshikimate-3-phosphate synthase, said enzyme being susceptible to inhibition of its enzymatic activity by the herbicidal agent glyphosate, the process comprising administering to said animal subject a therapeutically or prophylactically effective amount of a glyphosate source and a dicarboxylic acid source.

2. The process of claim 1 wherein the dicarboxylic acid is oxalic acid or a salt thereof.

3. The process of claim 1 wherein the glyphosate source is a salt of glyphosate.

4. The process of claim 1 wherein the glyphosate source is an ester of glyphosate.

5. The process of claim 1 wherein said subject is mammal.

6. The process of claim 1 wherein said subject is human.

7. The process of claim 1 wherein the glyphosate source is administered intravenously.

8. The process of claim 1 wherein the glyphosate source is administered orally.

* * * * *

UNITED STATES PATENT AND TRADEMARK OFFICE
CERTIFICATE OF CORRECTION

| | | |
|---|---|---|
| PATENT NO. | : 7,771,736 B2 | |
| APPLICATION NO. | : 10/652684 | |
| DATED | : August 10, 2010 | |
| INVENTOR(S) | : Abraham | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1672 days.

Signed and Sealed this
Twenty-second Day of March, 2011

David J. Kappos
*Director of the United States Patent and Trademark Office*